US006391228B1

(12) United States Patent
Berger et al.

(10) Patent No.: US 6,391,228 B1
(45) Date of Patent: May 21, 2002

(54) DIELECTRIC COMPOSITION HAVING AN IMPROVED GAS ABSORPTION

(75) Inventors: Noëlle Berger, Ecully; Raymond Commandeur, Vizille, both of (FR)

(73) Assignee: Atofina, Puteau (FR)

( * ) Notice: Subject to any disclaimer, the term of this patent is extended or adjusted under 35 U.S.C. 154(b) by 79 days.

(21) Appl. No.: 09/588,647

(22) Filed: Jun. 7, 2000

(30) Foreign Application Priority Data

Jun. 7, 1999 (FR) ........................................... 99 07143
Feb. 16, 2000 (FR) ........................................... 00 01880

(51) Int. Cl.$^{7}$ ................................................. C07C 1/16
(52) U.S. Cl. ......................... 252/570; 252/63; 252/581; 252/500; 585/19; 585/25
(58) Field of Search ................................ 252/570, 500, 252/62, 581; 585/19, 25

(56) References Cited

U.S. PATENT DOCUMENTS

| | | | | |
|---|---|---|---|---|
| 4,189,391 | A | 2/1980 | Kimura et al. | 252/63 |
| 5,446,228 | A | 8/1995 | Commandeur et al. | 585/6.3 |
| 5,601,755 | A | 2/1997 | Commandeur et al. | 252/570 |

FOREIGN PATENT DOCUMENTS

| | | |
|---|---|---|
| EP | 0 443 899 | 8/1991 |
| EP | 0 446 086 | 9/1991 |
| EP | 0 544 571 | 6/1993 |

*Primary Examiner*—Gregory Delcotto
*Assistant Examiner*—Derrick G Hamlin
(74) *Attorney, Agent, or Firm*—Millen, White, Zelano & Branigan, P.C.

(57) ABSTRACT

The invention relates to a dielectric composition having improved gas absorption for electrical devices which comprises from 99% to 70% by weight of a mineral oil and from 1% to 30% by weight of at least one polyarylalkane composition.

10 Claims, No Drawings

DIELECTRIC COMPOSITION HAVING AN IMPROVED GAS ABSORPTION

The present invention relates to a dielectric composition based on a mineral oil for electrical equipment having an improved gas absorption.

Mineral oils are widely used as insulating oils in various electrical devices, such as transformers, capacitors and cables.

These mineral oils comprise compounds of different natures, such as paraffin chains, saturated cyclic compounds, denoted as naphthenic compounds, or aromatic structures, including condensed polyaromatics.

Aromatic compounds bestow better dielectric properties, such as better breakdown voltage or so-called gassing properties, on the mineral oils.

The gas absorption is characteristic of the behaviour of an oil under a high electric field.

In the presence of gaseous hydrogen, the oil can either produce more gas, in which case it is said to be gas evolving, or can absorb the hydrogen; it is then said to be gas absorbing.

So-called gas absorbing oils are desired for electrical equipment.

Condensed polyaromatics are diverse and varied in nature but the majority are regarded as carcinogenic. Consequently, in order to reduce the content of polyaromatics in the mineral oils, the latter are subjected to a hydrogenation treatment. However, this treatment exhibits the disadvantage of resulting in the complete disappearance of the other aromatics regarded as not very toxic.

It has been discovered that the use of low amounts of compounds of the polyarylalkane family makes it possible to improve the gas absorption property of the mineral oils.

A subject-matter of the invention is therefore a dielectric composition for electrical devices, characterized in that it comprises from 99% to 70% by weight and preferably from 99% to 80% of a mineral oil and from 1% to 30% by weight and preferably from 1% to 20% of at least one polyarylalkane composition chosen from:

the compositions (I) comprising a mixture of products of formula (A):

(A)

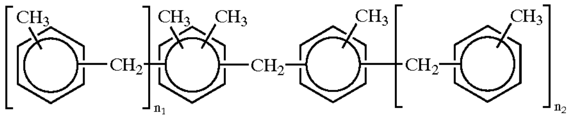

in which formula $n_1$, and $n_2$=0 or 1, which comprises products (A) such that $n_1+n_2=0$ and products (A) such that $n_1+n_2 1$, and of products of formula (B):

(B)

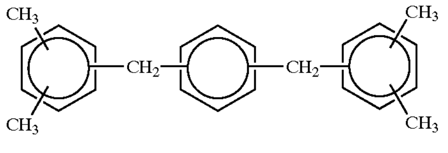

the compositions (II) comprising a mixture of two products (C) and (D), in which mixture:

the product (C) is a mixture of isomers of formula:

(C)

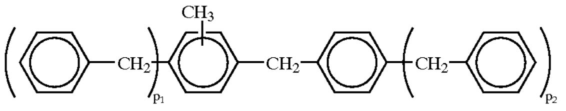

with $p_1$ and $p_2$=0, 1 and 2, and $p_1+p_2 \leqq 3$, and the product (D) is a mixture of isomers of formula:

(D)

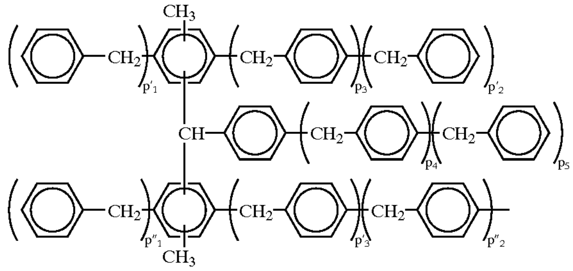

with $p'_1$, $p''_1$ and $p_4$=0, 1 and 2 $p'_2$, $p''_2$, $p_3$ and $p_5$=0 and 1, $p'_1+p''_1+p'_2+p''_2+p_3+p'_3+p_4+p_5 \leqq 2$, the compositions (III) comprising a mixture of two products (A1) and (A2), such that:

the product (A1) is a mixture of isomers of formula:

(A1)

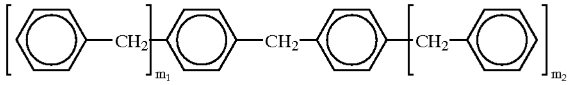

with $m_1$ and $m_2$=0, 1 or 2, and $m_1+m_2 \leqq 3$, the product (A2) is a mixture of isomers of formula:

(A2)

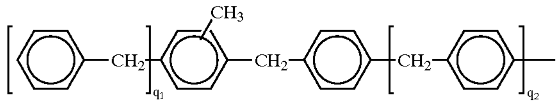

with $q_1$ and $q_2$=0, 1 or 2, and $q_1+q_2 \leqq 3$, at least one of the compounds (A1) and (A2) comprising an isomer having three benzene nuclei, the compositions (IV) comprising the two products (A1) and (A2) and, in addition, at least one compound chosen from the following products (E1), (E2) or (E3):

(E1) is an isomer or a mixture of isomers of formula:

(E1)

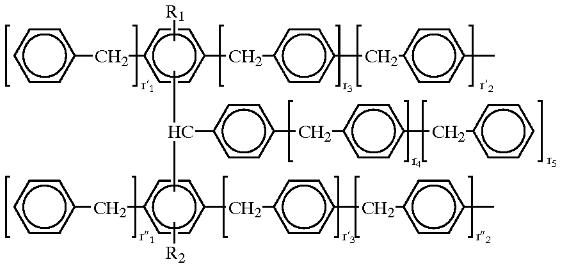

with $r'_1$, $r''_1$ and $r_4$=0, 1 or 2 $r'_2$, $r''_2$, $r_3$, $r'_3$ and $r_5$=0 and 1, and, $r'_1+r''_1+r'_2+r''_2+r_3+r'_3+r_4+r_5$ is less than or equal to 2, $R_1$ and $R_2$ represent a hydrogen atom, (E2) is an isomer or a mixture of isomers with the same general formula as (E1), except that $R_1$ and $R_2$ represent a methyl and the coefficients r are replaced by s and have the same meaning, (E3) is an isomer or a mixture of isomers with the same general formula as (E1), except that $R_1$ and $R_2$ are different and represent a hydrogen atom or a methyl radical and the coefficients r are replaced by t and have the same meaning.

According to the present invention, the compositions (I) can comprise product (A) comprising 2 nuclei, (methylbenzyl)xylene, and product (A) comprising 3 nuclei, which is denoted by bis(methylbenzyl)xylene. This product (A) comprising 3 nuclei can be product such that $n_1$=1 and $n_2$=0, product such that $n_1$=0 and $n_2$=1, or a mixture of these last two. The polyarylalkane composition can also comprise products such that $n_1$=1 and $n_2$=1.

Mention will be made, by way of illustration of compositions (I) which can be used according to the present invention, of the polyarylalkane composition sold by the Company Elf Atochem S.A. under the name Jarisol XX, which has a content by weight of compounds comprising 2 and 3 aromatic nuclei of greater than 99%.

Mention will be made, by way of illustration of compounds (II) which can be used according to the present invention, of the polyarylalkane composition sold by the Company Elf Atochem S.A. under the name Jarylec C100, which is composed essentially of 70% to 80% by weight of a mixture of benzyltoluene isomers (product (C), $p_1=p_2=0$) and of 20% to 30% by weight of dibenzyltoluene isomers (product (C), $p_1$=1, $p_2$=0 or $p_1$=0 and $p_2$=1) and of ditolylphenylmethane isomers (product (D), $p'_1+p''_1+p'_2+p''_2+p_3+p'_3+p_4+p_5=0$).

These compositions can be obtained by processes disclosed in Patents EP 136,230-B1, EP 299,867-B1, EP 384, 818-B1 and EP 500,435-B1, incorporated in the present invention by reference, which consist in chlorinating toluene or xylene and then carrying out a condensation of Friedel-Crafts type either on toluene or on xylene (mixture of isomers) or on a toluene and xylene mixture or on benzene or on a benzene and toluene mixture. On completion of the reaction, the unconverted reactant or reactants is/are removed directly by distillation and then the crude product can be subjected to a dechlorination treatment, such as disclosed in Patent EP 306,398-B1.

Thus, for example, the compositions (II) can be obtained by a process disclosed in Patent EP 136,230-B1 which consists, in a first stage, in reacting chlorine with toluene by a radical reaction in the presence of a free radical generator at a temperature of between 50° C. and 110° C. and then, in a second stage, the reaction product from the first stage is subjected to a condensation reaction with toluene in the presence of $FeCl_3$ at a temperature of between 50° C. and 100° C.

The compositions (I) can be obtained according to a process disclosed in Patent EP 050,435-B1 which consists in condensing (methyl)benzyl chloride with xylene in the presence of $FeCl_3$.

The dielectric compositions according to the invention exhibit the advantage of having an improved gaseous behaviour (improved gassing).

The examples which follow illustrate the invention.

The gassing property was evaluated using the method described in Standard 628 of the International Electrotechnical Commission (IEC).

According to this method, the interface between a column of liquid and a volume of hydrogen is subjected to a electrical discharge between 2 electrodes placed at different potentials.

The change in the volume of gas as a function of the time is monitored.

The gassing, expressed in $\mu$l/min, is positive if gas is released and is negative if gas is absorbed.

Various mixtures of a gas-evolving mineral oil of paraffin type and of the product Jarisol XX (hereinafter denoted by XX) were prepared and then evaluated at 80° C. according to the IEC 628-A method.

The gassing results are reported in Table 1.

TABLE 1

| COMPOSITION (% BY WEIGHT) | | GASSING |
|---|---|---|
| Mineral oil | XX | IN $\mu$l/min |
| 100% | — | +5.4 |
| 98% | 2% | −5 |
| 95% | 5% | −12.8 |
| 90% | 10% | −22.7 |

Various mixtures of more or less hydrogenated gas-evolving mineral oils of napthenic type (positive gassing) and of the product Jarylec C100 (hereinafter denoted by C100) were prepared and were then evaluated at 80° C. according to the IEC 628-A method.

The gassing results are reported in Table 2.

TABLE 2

| COMPOSITION (% BY WEIGHT) | | GASSING |
|---|---|---|
| | C100 | (IN $\mu$l/MIN) |
| Mineral oil X | | |
| 100% | | +3 |
| 99% | 1% | +0.4 |
| 98% | 2% | −0.4 |
| 97% | 3% | −5 |
| Mineral oil Y | | |
| 100% | — | +30 |
| 92% | 8% | −24 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French applications 99/07143 and 00/01880, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Dielectric composition for electrical devices, comprising from 99% to 70% by weight of a mineral oil and from 1% to 30% by weight of at least one polyarylalkane composition chosen from:

the compositions (I) comprising a mixture of products of formula (A):

(A)

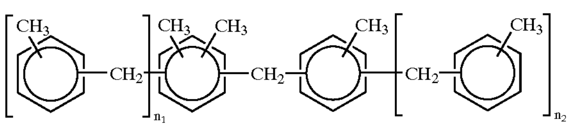

in which formula $n_1$ and $n_2$=0 or 1, which comprises products (A) such that $n_1+n_2=0$ and products (A) such that $n_1+n_2=1$, and of products of formula (B):

(B)

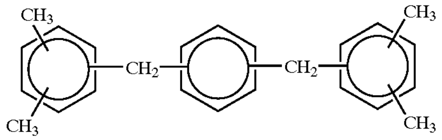

the compositions (II) comprising a mixture of two products (C) and (D), in which mixture:

the product (C) is a mixture of isomers of formula:

(C)

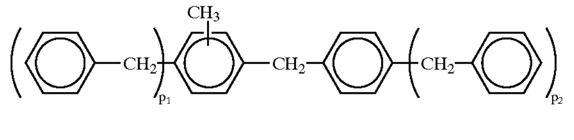

with $p_1$ and $p_2$=0, 1 and 2, and $p_1+p_2 \leqq 3$, and the product (D) is a mixture of isomers of formula:

(D)

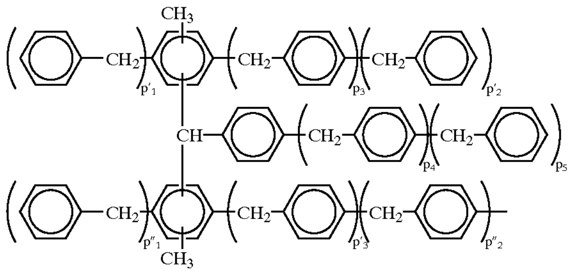

with $p'_1$, $p''_1$ and $p_4$=0, 1 and 2 $p'_2$, $p''_2$, $p_3$ and $p_5$=0 and 1 it being known that $p'_1+p''_{1+p'2}+p''_2+p_3+p'_3 +p_4+p_5 \leqq 2$, the compositions (III) comprising a mixture of two products (A1) and (A2), such that:

the product (A1) is a mixture of isomers of formula:

(A1)

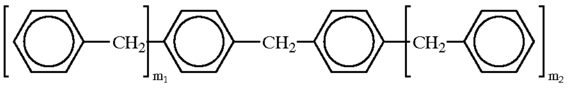

with $m_1$ and $m_2$=0, 1 or 2, it being known that $m_1+m_2 \leqq 3$, the product (A2) is a mixture of isomers of formula:

(A2)

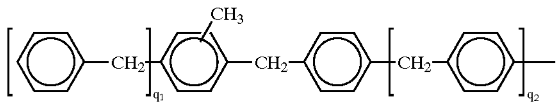

with $q_1$ and $q_2$=0, 1 or 2, it being known that $q_1+q_2 \leqq 3$, at least one of the compounds (A1) and (A2) comprising an isomer having three benzene nuclei, the compositions (IV) comprising the two products (A1) and (A2) and, in addition, at least one compound chosen from the following products (E1), (E2) or (E3);

(E1) is an isomer or a mixture of isomers of formula:

(E1)

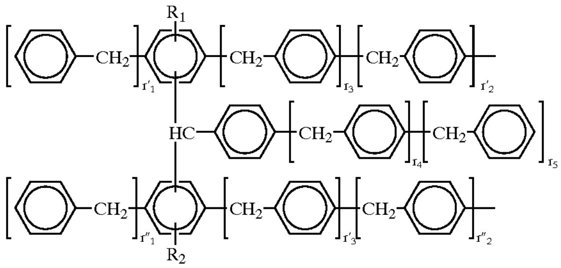

with $r'_1$, $r''_1$ and $r_4$=0, 1 or 2 $r'_2$, $r''_2$, $r_3$, $r'_3$ and $r_5$=0 and 1 it being known that $r'_1+r''_1+r'_2+r''_2+r_3+r'_3+r_4+r_5$ is less than or equal to 2, $R_1$ and $R_2$ represent a hydrogen atom, (E2) is an isomer or a mixture of isomers with the same general formula as (E1), except that $R_1$ and $R_2$ represent a methyl and the coefficients r are replaced by s and have the same meaning, (E3) is an isomer or a mixture of isomers with the same general formula as (E1), except that $R_1$ and $R_2$ are different and represent a hydrogen atom or a methyl radical and the coefficients r are replaced by t and have the same meaning.

2. A dielectric composition according to claim 1, comprising said compositions (I).

3. A dielectric composition according to claim 1, comprising said compositions (II).

4. A dielectric composition according to claim 1, comprising from 99% to 80% by weight of a mineral oil and from 1% to 20% by weight of at least one polyarylalkane composition chosen from the compositions (I), (II), (III) or (IV).

5. A dielectric composition according to claim 1, comprising said composition III.

6. A dielectric composition according to claim 1, comprising said composition IV.

7. A dielectric composition according to claim 2, having a content by weight of compounds comprising 2 and 3 aromatic nuclei of greater than 99%.

8. A dielectric composition according to claim 3, wherein said compositions II are composed essentially of 70% to 80% by weight of a mixture of benzyltoluene isomers (product (C), $p_1=p_2=0$) and of 20% to 30% by weight of dibenzyltoluene isomers (product (C), $p_1=1$, $p_2=0$ or $p_1=0$, $p_2=1$) and of ditolylphenylmethane isomers.

9. In an electrical device comprising at least one insulating oil, the improvement wherein said insulating oil consists essentially of a dielectric composition according to claim 1.

10. A device according to claim 9, being a transformer, capacitor or cable.

* * * * *

UNITED STATES PATENT AND TRADEMARK OFFICE

CERTIFICATE OF CORRECTION

PATENT NO. : 6,391,228 B1
DATED : May 21, 2002
INVENTOR(S) : Berger et al.

It is certified that error appears in the above-identified patent and that said Letters Patent is hereby corrected as shown below:

Title page,
Item [73], Assignee, “Puteau” should be -- Puteaux --

Column 5,
Line 66, “$p'_2$” should be -- $\mathrm{p}'_2$ --.

Column 6,
Lines 12 and 45, “it being known that” should be -- and --.

Signed and Sealed this

Twenty-second Day of March, 2005

JON W. DUDAS
*Director of the United States Patent and Trademark Office*